United States Patent

Schwarz et al.

[11] Patent Number: 4,611,010

[45] Date of Patent: Sep. 9, 1986

[54] HALOVINYLBENZYL ESTERS AND THEIR USE FOR CONTROLLING PESTS

[75] Inventors: Gerd-Ulrich Schwarz, Schifferstadt; Hans Theobald; Heinrich Adolphi, both of Limburgerhof, all of Fed. Rep. of Germany

[73] Assignee: BASF Aktiengesellschaft, Ludwigshafen, Fed. Rep. of Germany

[21] Appl. No.: 732,276

[22] Filed: May 9, 1985

[30] Foreign Application Priority Data

May 14, 1984 [DE] Fed. Rep. of Germany ....... 3417791

[51] Int. Cl.⁴ .................... A01N 37/34; A01N 53/00; C07C 121/66
[52] U.S. Cl. .................... 514/521; 514/531; 514/532; 514/538; 514/544; 558/406; 558/407; 558/414; 560/8; 560/55; 560/105; 560/124
[58] Field of Search .................. 260/465 D; 560/124, 560/8, 55, 105, 124; 558/406, 407, 414; 514/521, 531, 532, 538, 544

[56] References Cited

U.S. PATENT DOCUMENTS

| | | | |
|---|---|---|---|
| 4,091,110 | 5/1978 | Punja | 424/304 |
| 4,291,056 | 9/1981 | Meyer et al. | 424/304 |
| 4,423,064 | 12/1983 | Wheeler | 424/304 |

Primary Examiner—Dolph H. Torrence
Attorney, Agent, or Firm—Keil & Weinkauf

[57] ABSTRACT

Halovinylbenzyl esters of the formula I

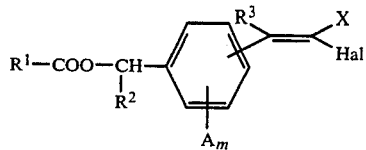

where $R^1$ is

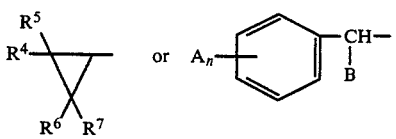

$R^2$ is H, CN, lower alkyl, lower alkenyl, lower alkynyl, lower haloalkyl or lower haloalkenyl, $R^3$ is H, halogen or lower alkyl, $R^4$ is H, lower alkyl, lower alkoxy or lower alkoxymethyl, $R^5$ is lower alkyl, lower halk(enyl or lower haloalkynyl, $R^6$ and $R^7$ are each lower alkyl or halogen, A is halogen, lower alkyl, lower alkoxy, lower haloalkyl, lower haloalkoxy, CN or $NO_2$, m is 0 to 4, n is 1 to 3, B is lower alkyl, lower alkenyl, lower alkynyl or cycloalkyl, and X is H, halogen, lower haloalkyl, lower thioalkyl, lower alkoxy or lower alkyl, and halogen can be fluorine, chlorine or bromine and, in the case of $R^2$, may furthermore be iodine, a process for their manufacture, and their use as pesticides.

3 Claims, No Drawings

HALOVINYLBENZYL ESTERS AND THEIR USE FOR CONTROLLING PESTS

It has been disclosed that 2,2-dimethyl-3-(2',2'-dimethylvinyl)-cyclopropane carboxylates whose ester group is a substituted vinylbenzyl radical possess insecticidal activity (GB Pat. No. 2,065,475 and BE Pat. No. 0,738,112).

The combination of such benzyl alcohols with specific carboxylic acids leads to pesticides having a particularly good action.

We have found that novel esters of the formula I

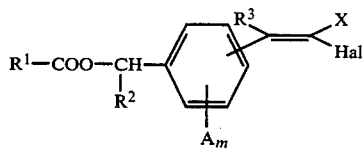

where $R^1$ is

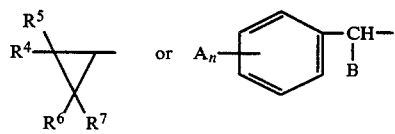

$R^2$ is H, CN, lower alkyl, lower alkenyl, lower alkynyl, lower haloalkyl or lower haloalkenyl, $R^3$ is H, halogen or lower alkyl, $R^4$ is H, lower alkyl, lower alkoxy or lower alkoxymethyl, $R^5$ is lower alkyl, lower haloalk(en)yl or lower haloalkynyl, $R^6$ and $R^7$ are each lower alkyl or halogen, A is halogen, lower alkyl, lower alkoxy, lower haloalkyl, lower haloalkoxy, CN or $NO_2$, m is 0 to 4, n is 1 to 3, B is lower alkyl, lower alkenyl, lower alkynyl or cycloalkyl, and X is H, halogen, lower haloalkyl, lower thioalkyl, lower alkoxy or lower alkyl, and halogen can be fluorine, chlorine or bromine and, in the case of $R^2$, may furthermore be iodine, possess particularly good insecticidal activity.

In formula I, $R^1$ is trisubstituted or polysubstituted cyclopropyl, in particular 3-(2,2-dihalovinyl)-2,2-dimethylcyclopropyl, eg. 3-(2,2-dichlorovinyl)-2,2-dimethylcyclopropyl, 3-(2,2-dibromovinyl)-2,2-dimethylcyclopropyl or 3-(2,2-difluorovinyl)-2,2-dimethylcyclopropyl; 3-(2-haloethynyl)-2,2-dimethylcyclopropyl, eg. 3-(2-chloroethynyl)-2,2-dimethylcyclopropyl or 3-(2-bromoethynyl)-2,2-dimethylcyclopropyl; 3-alkoxy-2,2-dimethylcyclopropyl, eg. 3-ethoxy-2,2-dimethylcyclopropyl, 3-alkoxymethyl-2,2-dimethylcyclopropyl, eg. 3-methoxymethyl-2,2-dimethylcyclopropyl; tetraalkylcyclopropyl, in particular tetramethylcyclopropyl; 3,3-dihalo-2,2-dialkylcyclopropyl, in particular 3,3-dichloro-2,2-dimethylcyclopropyl or 3,3-dibromo-2,2-dimethylcyclopropyl; or 3-(haloalkyl)-2,2-dimethylcyclopropyl, eg. 3-(tetrabromoethyl)-2,2-dimethylcyclopropyl or 3-(2,2-dichloro-1,2-dibromoethyl)-2,2-dimethylcyclopropyl, or a radical of the formula

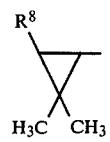

where $R^8$ is propen-2-yl, isobutenyl or 3-methylbuten-2-yl.

$R^1$ may furthermore be a radical of the formula

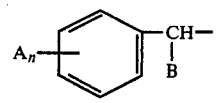

where n is 1 to 3, preferably 1, and substituents A are identical or different where there are two or three of these. In this case, A can be, for example, fluorine, chlorine or bromine, halomethyl, eg. trifluoromethyl, difluoromethyl or trichloromethyl, halomethoxy, eg. difluoromethoxy or trifluoromethoxy, cyano, nitro, or straight-chain or branched alkyl or alkoxy of not more than 3 carbon atoms, eg. methyl, methoxy, ethyl, ethoxy, n-propyl, isopropyl, n-propoxy or isopropoxy.

Where it occurs in substituent $R^1$, A is preferably haloalkoxy or halogen in the 4-position.

B can be straight-chain or branched alkyl, alkenyl or alkynyl of not more than 4 carbon atoms, eg. methyl, ethyl or, in particular, isopropyl, and furthermore tert.-butyl, isobutyl, allyl, isopropenyl, propargyl or an alicyclic radical of, for example, 3 to 7 carbon atoms, eg. cyclohexyl or, in particular, cyclopropyl or a heterocyclic radical containing not more than 3 heteroatoms (N or O).

$R^2$ is hydrogen, cyano, straight-chain or branched alkyl, alkeny, alkynyl, haloalkyl or haloalkenyl of not more than 3 carbon atoms, eg. methyl, ethyl, n-propyl, isopropyl, vinyl, allyl, n-propenyl, isopropenyl, ethynyl, n-propynyl, isopropynyl, trifluoromethyl, trichloromethyl, difluorovinyl or halogen, in particular iodine.

In formula I, A is hydrogen, radicals $A_m$ are not more than four substituents selected independently of one another, and radicals $A_n$ are not more than 3 such substituents, ie. halogen, such as fluorine, chlorine or bromine, straight-chain or branched alkyl, alkoxy, alkenyl or alkynyl of not more than 5, preferably not more than 3, carbon atoms, eg. methyl, ethyl, propyl, isopropyl, n-butyl, tert.-butyl, isobutyl or pentyl; methoxy, ethoxy, n-propoxy, isopropoxy, butoxy or pentyloxy; vinyl, allyl, n-propenyl, isopropenyl, n-butenyl, n-pentenyl, 1-methyl-n-propenyl, or 1-methyl-n-butenyl; ethynyl, n-propynyl, isopropynyl, n-butynyl, n-pentynyl, 1-methylpropynyl or 1-methylbutynyl; or CN or $NO_2$.

$R^3$ is, in particular, hydrogen, but may furthermore be halogen, such as fluorine, chlorine or bromine, or methyl, ethyl, propyl or isopropyl.

X is hydrogen or, preferably, halogen, such as fluorine or, in particular, chlorine or bromine, and may furthermore be, for example, methyl, ethyl, propyl, isopropyl, methoxy, ethoxy, thiomethyl, chloromethyl, bromomethyl, trifluoromethyl or trichloromethyl.

In each case, the compounds of the formula I can of course occur as one or more pairs of optical antipodes, and in many case also in the form of a large number of diastereomers; these occur in pure form or as mixtures, depending on the starting materials and the reaction conditions. The mixtures can be separated into their sterically pure components in a conventional manner; in specific cases, their biological action depends on their steric configuration.

The esters of the formula I can be obtained by reacting the corresponding acyl halides with appropriate halovinylbenzyl alcohols in the presence of an acid acceptor.

The esters can of course also be prepared from the corresponding carboxylic acids and the corresponding halovinylbenzyl halides in the presence of an acid acceptor.

Finally, the novel esters may also be obtained from the free carboxylic acids and alcohols under esterification conditions, or by reacting available esters with appropriate carboxylic acids or alcohols under transesterification conditions.

Some of the carboxylic acid halides or free carboxylic acids or carboxylic acids required are disclosed in British Pat. No. 1,446,304 and U.S. Pat. No. 3,981,903. Where in a specific case they are novel, they may be prepared in a conventional manner using the halovinylbenzyl compounds which are required and essential according to the invention (cf. German Laid-Open Applications DOS 2,633,551 and DOS 3,329,288), for example in order to introduce the halovinyl radical into the benzyl radical, by reaction of an aldehyde with an appropriate Wittig reagent or by hydroboration or hydroaluminum or hydrogen halide addition at alkynes (Houben-Weyl, Methoden der organischen Chemie, 4th edition, Vol. V/1 b, page 795 et seq.). Some of the intermediates required for the preparation of the active ingredients are known and some are novel; they can in any case be prepared by a conventional process. In this context, reference may be made to, for example, U.S. Pat. Nos. 3,979,519 and 3,981,903, Belgian Pat. No. 801,946 and German Laid-Open Applications DOS 2,365,555 and DOS 2,231,312.

Some or all of the benzyl halides, alcohols and aldehydes required for the novel esters of the formula I are novel.

They can be prepared from the corresponding haloaromatics, toluenes or benzoic acids, some of which are known, by a conventional method, for example halogenation with N-bromosuccinimide, reduction of acids or esters, or oxidation of alcohols.

The preparation of these haloaromatics, toluenes or benzoic acids is described in, for example, GB Pat. No. 2,078,238; JA Pat. No. 4,791,900-Q; U.S. Pat. No. 3,336,335; EP Pat. No. 53,687; EP Pat. No. 35,724; Z. org. Chim. 1965, 1998-2002; Liebigs Ann. Chem. 1980, 2061-2071; J. Org. Chem. 36, 1438-1440 (1971); J. Am. Chem. Soc. 1983, 2388-93.

EXAMPLES OF THE PREPARATION OF THE NOVEL BENZYL HALIDES, ALCOHOLS AND ALDEHYDES

A. 2-(2,2-Dichlorovinyl)-benzyl bromide 211 g (1.13 moles) of 2-(2,2-dichlorovinyl)-toluene, 251 g (1.41 moles) of N-bromosuccinimide and 2 g of azoisobutyronitrile in 1300 ml of dry 1,1,1-trichloroethane are refluxed, an additional 1 g of azoisobutyronitrile is added to the reaction mixture after one hour, and heating is continued for a further hour.

The mixture is cooled and filtered over silica gel, the solution is evaporated down and the residue is subjected to fractional distillation under 0.05 mm Hg.

A pale liquid of refractive index $n_D^{23}$ 1.6070 is obtained at from 95° to 97° C., in a yield of 258.6 g.

Theory: C, 40.64; H, 2.65; Cl, 26.66; Br, 30.04. Found: C, 40.1; H, 2.9; Cl, 26.5; Br, 30.5.

B. 2-(2,2-Dichlorovinyl)-benzyl acetate 235 g (0.88 mole) of 2-(2,2-dichlorovinyl)-benzyl bromide and 144 g (1.76 moles) of Na acetate are suspended in 220 ml of glacial acetic acid and 300 ml of dimethylformamide, and the suspension is stirred with 2 g of KI for 5 hours at 140° C.

The mixture is allowed to cool, and $H_2O$ and ether are added while stirring. The ether is separated off and the aqueous phase is once again extracted by shaking with ether. The combined ether phases are washed with $NaHCO_3$ solution and water, dried and evaporated down, the oily product is taken up with toluene, the solution is filtered over silica gel, and the filtrate is evaporated down to give a pale yellow oil of refractive index $n_D^{23}$ 1.5484, in a yield of 135 g.

Theory: C, 53.60; H, 4.11 O, 13.06; Cl, 28.93. Found: C, 53.6; H, 4.3 O, 13.3; Cl, 28.7.

C. 2-(2,2-Dichlorovinyl)-benzyl alcohol 133 g (0.54 mole) of 2-(2,2-dichlorovinyl)-benzyl acetate are dissolved in 200 ml of ethanol, and the solution is added, at room temperature, to 750 ml of an ethanolic KOH solution saturated at room temperature. After 2 hours, the mixture is evaporated down, the residue is taken up with $H_2O$, the solution is extracted several times by shaking with ether, and the combined ether phases are washed with $H_2O$, dried and evaporated down.

A pale yellow oil of refractive index $n_D^{21}$ 1.5891 is obtained in a yield of 105 g.

Theory: C, 53.23; H, 3.97; O, 7.88; Cl, 34.92. Found: C, 53.0; H, 4.0; O, 7.6; Cl, 35.1.

D. 2-(2,2-Dichlorovinyl)-benzaldehyde 20.3 g (0.1 mole) of 2-(2,2-dichlorovinyl)-benzyl alcohol are added to a mixture of 15.7 g (0.16 mole) of concentrated $H_2SO_4$ and 19.8 g (1.1 moles) of $H_2O$, the mixture is heated to 60° C., and a solution of 11.9 g (0.04 mole) of $Na_2Cr_2O_7$ in 8 ml of $H_2O$ is added dropwise in such a manner that the temperature increases to 100° C. Stirring is continued at this temperature for half an hour, after which the mixture is cooled, 20 ml of $H_2O$ are added and extraction by shaking with toluene is carried out several times. The toluene solutions are combined, and filtered over silica gel, and the filtrate is evaporated down.

A pale oil of refractive index $n_D^{22}$ 1.5983 is obtained in a yield of 13.1 g.

Theory: C, 53.77; H, 3.01; O, 7.96; Cl, 35.27. Found: C, 53.5; H, 3.3; O, 7.7; Cl, 35.4.

E. 2-(2,2-Dichlorovinyl)-(γ-isopropyl)-benzyl alcohol 3.6 g (0.15 mole) of Mg turnings are covered with a layer of 10 ml of absolute ether. 18.5 g (0.15 mole) of 2-bromopropane in 50 ml of absolute ether are added dropwise in such a manner that the mixture boils gently. Stirring is continued for 1 hour at this temperature, after which the mixture is cooled to room temperature. 15 g (0.075 mole) of 2-(2,2-dichlorovinyl)-benzaldehyde in 50 ml of ether are then slowly added dropwise, stirring is continued for 1 hour at 40° C., the mixture is cooled to 0° C. and 150 ml of $NH_4Cl$ solution are slowly added.

The ether phase is separated off, washed with NaHCO$_3$ solution and water, dried and evaporated down.

The oil which remains is separated by column chromatography over silica gel, using a 9:1 toluene/acetone mixture is eluent. 12 g of a pale yellow oil are obtained.

Theory: C, 58.31; H, 6.52; O, 6.47; Cl, 28.69. Found: C, 58.6; H, 6.2; O, 6.9; Cl, 28.5

PREPARATION EXAMPLE 1

3-(2,2-Dibromovinyl)-α-cyanobenzyl 3-(2,2-dichlorovinyl)-2,2-dimethylcyclopropanecarboxylate In a two-phase reaction mixture, 6.1 g (0.021 mole) of 3-(2,2-dibromovinyl)-benzaldehyde in 50 ml of ether, 1.5 g (0.023 mole) of KCN in 20 ml of water, 5.0 g (0.022 mole) of 3-(2,2-dichlorovinyl)-2,2-dimethylcyclopropanecarboxylic acid chloride and 0.5 g of triethylbenzylammonium chloride are stirred at room temperature, and thorough mixing is continued overnight at 25° C. The phases are separated and the aqueous phase is extracted twice by shaking with ether. The ether solution is washed with sodium bisulfite, NaHCO$_3$ and water, dried over Na$_2$SO$_4$ and evaporated down.

9.1 g (yield 91%) of a yellowish oil is obtained which is purified over a silica gel column, using toluene as eluent.

Calculated: C, 42.56; H, 2.98; O, 6.30; N, 2.76; Cl, 13.96; Br, 31.46. Found: C, 42.6; H, 3.0; O, 5.9; N, 2.7; Cl, 13.5; Br, 31.6. $n_D^{23}$: 1.5880.

PREPARATION EXAMPLE 2

2-(2,2-dichlorovinyl)-benzyl 2-(4-chlorophenyl)-isovalerate 2.8 g (0.012 mole) of 2-(4-chlorophenyl)-isovaleryl chloride in 50 ml of absolute toluene are introduced into 1.2 g (0.013 mole) of -picoline and 3.2 g (0.015 mole) of 2-(2,2-dichlorovinyl)-benzaldehyde in a conical flask at room temperature, while stirring. After 30 minutes, the mixture is filtered under suction over silica gel, and washing is carried out with toluene.

The filtrate is evaporated down to give 3.9 g (82% yield) of an oil of refractive index $n_D^{21}$ 1.5620.

Calculated: C, 60.40; H, 4.82; O, 8.05; Cl, 26.74. Found: C, 59.9; H, 4.8; O, 7.7; Cl, 26.4.

The compounds in the Table below which appear together with characteristic physical data were obtained by appropriately modifying the above preparation examples.

The compounds which have not been characterized can be obtained in the same manner from appropriate intermediates; because of their structural similarity to the compounds investigated in detail, they are expected to have a similar action.

TABLE 1

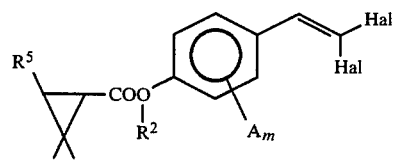

| No. | R$^5$ | R$^2$ | Hal | A$_m$ | $n_D$ [°C.] |
|---|---|---|---|---|---|
| 3 | Cl$_2$C=CH | H | Br | H | 1.5912 [22] |
| 4 | Cl$_2$C=CH | CN | Br | H | 1.6070 [23] |
| 5 | Cl$_2$C=CH | vinyl | Br | H | 1.5827 [23] |
| 6 | Cl$_2$C=CH | H | Cl | 2-F | 1.5628 [22] |
| 7 | Cl$_2$C=CH | H | Cl | 2-Cl, 6-Cl | 1.5765 [18] |
| 8 | Cl$_2$C=CH | H | Cl | 2 Cl | 1.5798 [22] |
| 9 | Cl$_2$C=CH | CN | Cl | 2 Cl | (viscous oil) |
| 10 | Cl$_2$C=CH | CN | Cl | H | 1.5740 [23] |
| 11 | Cl$_2$C=CH | H | Cl | H | 1.5764 [24] |
| 12 | Cl$_2$C=CH | vinyl | Cl | H | 1.5729 [21] |
| 13 | Cl$_2$C=CH | i-propyl | Cl | H | 1.5446 [21] |
| 14 | Cl$_2$C=CH | ethynyl | Cl | H |  |
| 15 | Cl$_2$C=CH | ethynyl | Cl | 2-Cl, 6-Cl |  |
| 16 | Cl$_2$C=CH | ethynyl | Cl | 2-F |  |
| 17 | (CH$_3$)$_2$C=CH | H | Br | H | 1.5734 [23] |
| 18 | (CH$_3$)$_2$C=CH | CN | Br | H | 1.5766 [23] |
| 19 | (CH$_3$)$_2$C=CH | CN | Cl | H | 1.5580 [23] |
| 20 | (CH$_3$)$_2$C=CH | H | Cl | H | 1.5560 [24] |
| 21 | (CH$_3$)$_2$C=CH | vinyl | Cl | H | 1.5440 [21] |
| 22 | (CH$_3$)$_2$C=CH | i-propyl | Br | H | 1.5332 [21] |
| 23 | (CH$_3$)$_2$C=CH | H | Cl | 2-Cl | 1.5648 |
| 24 | ClC≡C | H | Br | 2-F, 6-F | 1.5648 |
| 25 | BrC≡C | CN | Br | 2-Cl, 6-OCH$_3$ |  |
| 26 | BrC≡C | ethynyl | Cl | H |  |
| 27 | BrC≡C | CN | Cl | H |  |
| 28 | Br$_2$C=CH | vinyl | Cl | H | 1.5805 [21] |
| 29 | Br$_2$C=CH | i-propyl | Cl | H | 1.5606 [21] |
| 30 | Br$_2$C=CH | H | Cl | 2-Cl | 1.5981 [21] |
| 31 | Br$_2$C=CH | H | Cl | 2-Cl, 6-Cl | 1.5970 [20] |
| 32 | Br$_2$C=CH | H | Cl | 2-F | 1.5820 [23] |
| 33 | Br$_2$C=CH | H | Br | H | 1.6133 [23] |
| 34 | Br$_2$C=CH | ethynyl | Cl | H |  |
| 35 | Br$_3$C—CHBr | ethynyl | Cl | 2-F, 6-F |  |
| 36 | Cl$_2$BrC—CHBr | CN | Br | 2-F, 6-Cl |  |
| 37 | H | CN | Cl | H |  |

TABLE 2

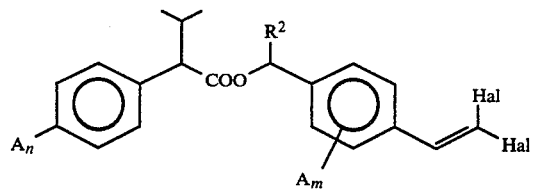

| No. | A$_n$ | R$^2$ | Hal | A$_m$ | $n_D$ [°C.] |
|---|---|---|---|---|---|
| 38 | Cl | H | Br | H | 1.5938 [23] |
| 39 | Cl | H | Cl | 2-F | 1.5660 [22] |
| 40 | Cl | H | Cl | 2-Cl | 1.5796 [22] |
| 41 | Cl | H | Cl | H | 1.5790 [24] |
| 42 | Cl | CN | Cl | H | 1.5739 [23] |
| 43 | Cl | vinyl | Cl | H | 1.5632 [21] |
| 44 | Cl | i-propyl | Cl | H | 1.5500 [21] |
| 45 | Cl | ethynyl | Cl | H |  |
| 46 | OCH$_3$ | H | Cl | 2-Br |  |
| 47 | OC$_2$H$_5$ | CN | Br | 2-F, 6-F |  |
| 48 | OCF$_3$ | H | F | 2-Cl, 3-Br |  |
| 49 | OCHF$_2$ | ethynyl | Cl | 2-F, 6-Cl |  |
| 50 | CH$_3$ | H | F | H |  |
| 51 | CHF$_2$ | CN | Cl | 2-CF$_3$ |  |

TABLE 3

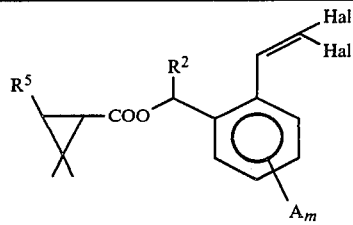

| No. | R⁵ | R² | Hal | $A_m$ | $n_D$ [°C.] |
|---|---|---|---|---|---|
| 52 | Cl₂C=CH | H | Br | H | 1.5797 [23] |
| 53 | Cl₂=CH | CN | Br | H | 1.5760 [23] |
| 54 | Cl₂C=CH | H | Cl | H | 1.5620 [21] |
| 55 | Cl₂C=CH | CN | Cl | H | 1.5575 [21] |
| 56 | Cl₂C=CH | i-propyl | Cl | H | 1.5398 [21] |
| 57 | Cl₂C=CH | ethynyl | Cl | H | |
| 58 | Cl₂C=CH | H | Cl | 4-CF₃ | |
| 59 | Cl₂C=CH | vinyl | Cl | 4-CH₃, 6-F | |
| 60 | Cl₂C=CH | CN | Br | 4-OCH₃, 6-Cl | |
| 61 | Br₂C=CH | H | Cl | H | 1.5827 [21] |
| 62 | Br₂C=CH | CN | Cl | H | 1.5768 [21] |
| 63 | (CH₃)₂C=CH | H | Cl | H | 1.5405 [21] |
| 64 | (CH₃)₂C=CH | CN | Cl | H | 1.5318 [21] |
| 65 | (CH₃)₂C=CH | i-propyl | Cl | H | 1.5426 [21] |
| 66 | (CH₃)₂C=CH | H | Br | H | 1.5797 [23] |
| 67 | (CH₃)₂C=CH | CN | Br | H | 1.5547 [23] |

TABLE 4

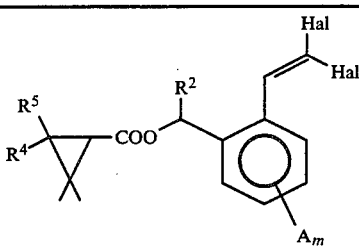

| No. | R⁵ | R² | Hal | $A_m$ | $n_D$ [°C.] |
|---|---|---|---|---|---|
| 68 | CH₃ | H | Cl | H | 1.5351 [22] |
| 69 | CH₃ | ethynyl | Cl | 4-C₂H₅ | |
| 70 | CH₃ | vinyl | Cl | 4-propargyl | |
| 71 | CH₃ | CN | Cl | 4-allyl | |
| 72 | CH₃ | i-propyl | Cl | 4-allyl | |
| 73 | CH₃ | H | Cl | CN | |
| 74 | CH₃ | H | Cl | NO₂ | |
| 75 | CH₃ | H | Cl | 4-dichlorovinyl | |
| 76 | Cl | H | Cl | H | 1.5541 [22] |
| 77 | Cl | ethynyl | Cl | H | |
| 78 | Cl | CN | Cl | H | |

TABLE 5

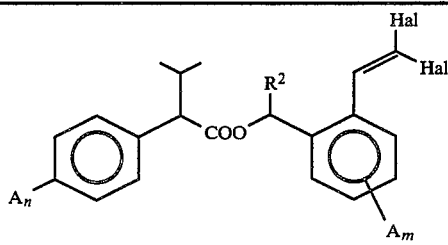

| No. | $A_n$ | R² | Hal | $A_m$ | $n_D$ [°C.] |
|---|---|---|---|---|---|
| 79 | Cl | H | Br | H | 1.5810 [23] |
| 80 | Cl | CN | Br | H | 1.5760 [23] |
| 81 | Cl | CN | Cl | H | 1.5588 [21] |
| 82 | Cl | i-propyl | Cl | H | 1.5579 [21] |
| 83 | Cl | ethynyl | Cl | H | |

TABLE 5-continued

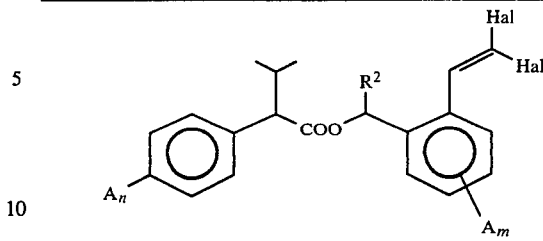

| No. | $A_n$ | R² | Hal | $A_m$ | $n_D$ [°C.] |
|---|---|---|---|---|---|
| 84 | OCF₃ | H | Cl | 4-ethynyl | |
| 85 | Cl | CN | Br | 4-dimethylvinyl | |

TABLE 6

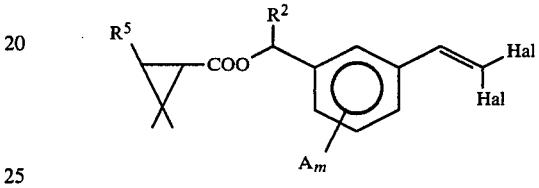

| No. | R⁵ | R² | Hal | $A_m$ | $n_D$ [°C.] |
|---|---|---|---|---|---|
| 86 | Cl₂C=CH | H | Cl | 2-Cl | 1.5789 [22] |
| 87 | Cl₂C=CH | H | Cl | H | 1.5728 [24] |
| 88 | Cl₂C=CH | CN | Cl | H | 1.5722 [23] |
| 89 | Cl₂C=CH | vinyl | Cl | H | 1.5627 [22] |
| 90 | Cl₂C=CH | i-propyl | Cl | H | 1.5420 [21] |
| 91 | Cl₂C=CH | CH₃ | Cl | H | viscous oil |
| 92 | Cl₂C=CH | H | Br | H | 1.5884 [22] |
| 93 | Cl₂C=CH | ethynyl | Cl | H | |
| 94 | BrC=C | CN | Cl | H | |
| 95 | Br₂C=CH | H | Br | H | 1.6090 [23] |
| 96 | Br₂C=CH | i-propyl | Cl | H | 1.5596 [21] |
| 97 | Br₂C=CH | ethynyl | Cl | H | |
| 98 | Br₂C=CH | H | Cl | 5-OCH₃, 6-Cl | |
| 99 | Br₂C=CH | H | Br | 5 CF₃ | |
| 100 | (CH₃)₂C=CH | H | Cl | 2-Cl | 1.5593 [22] |
| 101 | (CH₃)₂C=CH | H | Br | H | 1.5700 [23] |
| 102 | (CH₃)₂C=CH | H | Cl | H | 1.5761 [24] |
| 103 | (CH₃)₂C=CH | CN | Cl | H | 1.5558 [23] |
| 104 | (CH₃)₂C=CH | vinyl | Cl | H | 1.5462 [22] |
| 105 | (CH₃)₂C=CH | i-propyl | Cl | H | 1.5278 [21] |

TABLE 7

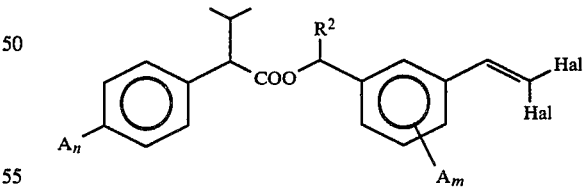

| No. | $A_n$ | R² | Hal | $A_m$ | $n_D$ [°C.] |
|---|---|---|---|---|---|
| 106 | Cl | H | Cl | H | 1.5537 [24] |
| 107 | Cl | i-propyl | Cl | H | 1.5444 [21] |
| 108 | Cl | H | Br | H | 1.5874 [22] |
| 109 | Cl | H | Cl | 2-Cl | 1.5812 [22] |
| 110 | Cl | ethynyl | Cl | H | |

The action of a representative selection of compounds on insects and mites is apparent from the following application examples.

The agent used for comparison purposes is the structurally close prior art commercial product Allethrin:

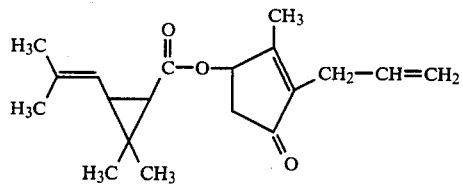

1. Continuous contact action on houseflies (Musca domestica)

Petri dishes 10 cm in diameter were lined with acetonic solutions of the active ingredients.

After the solvent had evaporated, 20 4-day old houseflies were placed in each dish.

The kill rate was determined after 4 hours.

| Ex. no. | mg | Kill % |
|---|---|---|
| 1 | 0.01 | 100 |
| 2 | 2.0 | 100 |
| 3 | 2.0 | 100 |
| 52 | 0.2 | 100 |
| 53 | 0.2 | 80 |
| 54 | 0.2 | 100 |
| 55 | 0.2 | 100 |
| 61 | 0.2 | 100 |
| 62 | 0.2 | 100 |
| 63 | 2.0 | 100 |
| 68 | 0.2 | 80 |
| 76 | 2.0 | 100 |
| 79 | 2.0 | 100 |
| 86 | 0.2 | 100 |
| 87 | 0.2 | 100 |
| 88 | 0.02 | 100 |
| 89 | 0.2 | 100 |
| 92 | 0.01 | 100 |
| 95 | 0.02 | 100 |
| 96 | 2.0 | 100 |
| 101 | 0.2 | 100 |
| 102 | 0.2 | 100 |
| 103 | 0.01 | 80 |
| 104 | 2.0 | 100 |
| 106 | 0.2 | 100 |
| 108 | 0.2 | 100 |

2. Contact action and effect of ingested food on caterpillars of the diamondback moth (Plutella maculipennis)

Leaves of young cabbage plants were dipped for 3 seconds in aqueous emulsions of the active ingredients. After excess liquid has been briefly allowed to drip off, the leaves were placed on a moist filter paper in a Petri dish. 10 caterpillars of the 4th stage were then placed on each leaf.

The action was assessed after 48 hours.

| Ex. no. | % | Kill % |
|---|---|---|
| 54 | 0.01 | 100 |
| 88 | 0.01 | 100 |
| 92 | 0.004 | 100 |
| Comparative agent | 0.02 | 100 |
|  | 0.01 | <70 |

3. Contact action on mosquito larvae (Aedes aegypti)

Formulations of the active ingredients were added to 200 ml of tapwater; 30 to 40 mosquito larvae in the 4th larval stage were then introduced.

The temperature was kept at 20° C. The action was assessed after 24 hours.

| Ex. no. | ppm | Kill % |
|---|---|---|
| 1 | 0.01 | 100 |
| 52 | 0.04 | 100 |
| 61 | 0.01 | 100 |
| 87 | 0.01 | 100 |
| 88 | 0.01 | 100 |
| 89 | 0.04 | 100 |
| 95 | 0.02 | 100 |
| Comparative agent | 0.1 | 100 |
|  | 0.04 | <60 |

4. Action on spider mites (Tetranychus telarius) (Test A)

Potted bush beans which had developed the first pair of true leaves and were under heavy attack from spider mites (Tetranychus telarius) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

| Ex. no. | % | Kill % |
|---|---|---|
| 54 | 0.04 | 100 |
| 63 | 0.02 | 100 |
| 68 | 0.02 | 100 |
| 106 | 0.05 | 100 |
| Comparative agent | 0.1 | <70 |

5. Continuous contact action on houseflies (Musca domestica)

Roughene glass plates 15×15 cm square were uniformly treated with acetonic solutions of the active ingredients. After the solvent had evaporated, 10 4-day old houseflies were placed on each glass plate under a Petri dish (10 cm diameter). The kill rate after 4 hours was used as a reference value in the experiment.

The tests were repeated daily until the treated plates had no more effect.

The temperature was kept at 20° to 22° C.

Results:

| | | | |
|---|---|---|---|
| Ex. 1 | 1 mg | 30 days | 100% kill |
| Ex. 95 | 1 mg | 30 days | 100% kill |
| Comparative agent | 1 mg | 4 days | 50% kill |

6. Contact action on ticks (Ornithodorus moubata)

The experiment was carried out on young ticks which had sucked blood only once. Commercially available tea-bags, each containing 5 animals, were dipped for 5 seconds in the aqueous active ingredient formulation. The bags were then suspended. The temperature was kept at 25° to 26° C. The kill rate was determined after 48 hours. Results:

| Ex. no. | % | Kill % |
|---|---|---|
| 1 | 0.04 | 100 |
| 52 | 0.1 | 100 |
| 54 | 0.04 | 100 |

| Ex. no. | % | Kill % |
| --- | --- | --- |
| 66 | 0.1 | 100 |
| 79 | 0.1 | 100 |
| 87 | 0.004 | 100 |
| 89 | 0.02 | 100 |
| 92 | 0.04 | 100 |
| 95 | 0.002 | 100 |
| 102 | 0.1 | 100 |
| 103 | 0.1 | 100 |
| 109 | 0.04 | 100 |

We claim:

1. Halovinylbenzyl esters of the formula

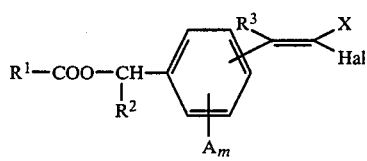

where $R^1$ is

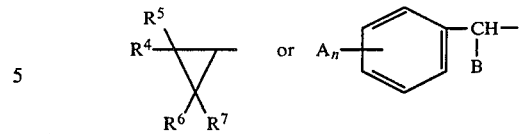

$R^2$ is H, CN, lower alkyl, lower alkenyl, lower alkynyl, lower haloalkyl or lower haloalkenyl, $R^3$ is H, halogen or lower alkyl, $R^4$ is H, lower alkyl, lower alkoxy or lower alkoxymethyl, $R^5$ is lower alkyl, lower haloalk(en)yl or lower haloalkynyl, $R^6$ and $R^7$ are each lower alkyl or halogen, A is halogen, lower alkyl, lower alkoxy, lower haloalkyl, lower haloalkoxy, CN or $NO_2$, m is 0 to 4, n is 1 to 3, B is lower alkyl, lower alkenyl, lower alkynyl or cycloalkyl, and X is H, halogen, lower haloalkyl, lower thioalkyl, lower alkoxy or lower alkyl, and halogen can be fluorine, chlorine or bromine and, in the case of $R^2$, may furthermore be iodine.

2. A pesticidal composition containing a solid or liquid carrier and an effective amount of at least one ester of the formula I as defined in claim 1.

3. A process for combatting pests, wherein an effective amount of at least one ester of the formula I as defined in claim 1 is allowed to act on the pests or their habitat.

* * * * *